United States Patent [19]

Baudier et al.

[11] Patent Number: 4,832,958

[45] Date of Patent: May 23, 1989

[54] GALENIC FORMS OF PROLONGED RELEASE VERAPAMIL AND MEDICAMENTS CONTAINING THEM

[75] Inventors: Philippe Baudier, Waterloo; Arthur De Boeck, Herne; Jacques Fossion, Braine-L'Alleud, all of Belgium

[73] Assignee: Pharlyse Societe Anonyme, Luxembourg Ville, Luxembourg

[21] Appl. No.: 913,279

[22] Filed: Sep. 30, 1986

[30] Foreign Application Priority Data

Sep. 30, 1985 [LU] Luxembourg ............................ 86099

[51] Int. Cl.[4] .......................... A61K 9/22; A61K 9/32; A61K 9/44
[52] U.S. Cl. .................................................... 424/473
[58] Field of Search ........................................ 424/473

[56] References Cited

PUBLICATIONS

Einig CA. 98: 59901w (1983) of Ger. Off. DE 3113901, Oct. 28, 1982.

Primary Examiner—Shep K. Rose
Attorney, Agent, or Firm—Sughrue, Mion, Zinn, Macpeak, and Seas

[57] ABSTRACT

The new galenic forms of prolonged release verapamil consist of microgranules containing a pharmacologically acceptable acid-addition salt or verapamil as active substance combined with at least one wetting agent, said microgranules being coated with a microporous membrane consisting of at least one pharmacologically acceptable adjuvant (such as plasticizer, filler, lubricant, etc) and of at least one film forming mixture composed of (1) at least one insoluble acrylic or methacrylic polymer and (2) a substance which is insoluble in the acid gastric medium, but soluble in the intestine.

32 Claims, 6 Drawing Sheets

GALENIC FORMS OF PROLONGED RELEASE VERAPAMIL AND MEDICAMENTS CONTAINING THEM

PRIOR ART

Verapamil, or 5-(3,4-dimethoxyphenylethyl)methylamino-2-(3,4-dimethoxyphenyl)-2-isopropyl valeronitrile corresponding to formula I, has been known for more than 20 years and its synthesis is described in Belgian Pat. No. 615 816 corresponding to the Dengel U.S. Pat. No. 3,261,859.

The hydrochloride of verapamil is used in medicine for its remarkable antagonistic properties against intracellular penetration of calcium. It is an important drug for the treatment of angina pectoris when the attack is associated with a coronary spasm and beta-adrenolytic products such as propanolol, timolol, atenolol and pindolol are liable to have undesirable effects. It is also useful in the treatment of hypertension and cardiac arrythmia.

It is known to the man of the art that the pharmacological action of verapamil is proportional to its concentration in the plasma (Br. J. Clin. Pharmac. (1981), 12, 397–400) and that the optimum therapeutic range extends from 100 ng/ml to 400 ng/ml of plasma.

The major disadvantage of treatment based on verapamil is that the half-life of this substance in the plasma is very short (2 to 4 hours) so that it requires the administration of several daily doses at intervals of only 6 hours. Such frequent administration renders the treatment difficult if not impossible to follow, especially during the night. Moreover, it has been found that after each administration of a quick-release galenic form of verapamil, that is to say generally four times per day, there follows a succession of rapid increases and decreases in the plasma level. The whole organism and especially the organ to be treated, in this case the heart, are thus subjected to alterning overdoses and underdoses of the medicament.

To obviate these disadvantages, a first prolonged release galenic form of verapamil, known as "Isoptine retard" (slow isoptine) has been brought on the market in the form of a tablet made up with a hydrophilic matrix. Although this galenic prolonged release form removes the concentration peaks, the bioavailability of verapamil from this galenic form is extremely low, as will be shown later, so that it is virtually impossible to obtain plasma levels within the optimum therapeutic zone and it is therefore difficult to produce the desired clinical effect.

Another type of galenic form, consisting of coated pellets or microgranules and also providing promonged release of verapamil, was subsequently developed (Copending U.S. patent application Ser. No. 909054 filed by the present Applicants on Sept. 18, 1986). Although this new type of galenic form has remarkable bioavailability combined with excellent prolonged-release kinetics of verapamil, the release kinetics are found to be unstable when the preparation is kept under severe conditions of high temperature, but such stability is absolutely essential for safe use of this type of preparation. In the course of stability tests to which these galenic forms according to the aforesaid U.S. patent application were subjected, that is is to say at temperatures comprised between 45° and 70° C., the release kinetics of verapamil were found to undergo considerable changes (see attached FIGS. 1, 2 and 3), manifesting both in a considerable reduction in the speed of release of verapamil and in incomplete release of the verapamil, the fraction released in some cases not exceeding 50% of the available dose.

This altered release has the following consequences:

1. The product no longer conforms to the standards of release determined "in vitro", so that when the drug is checked again, the batches which have undergone this change must be withdrawn from the market and/or destroyed by the manufacturer.

2. The altered product will no longer be capable of producing the expected therapeutic effect. This is all the more dangerous since the drug is used for cardiovacular purposes and the alteration cannot be detected by any visible change in the appearance of the product.

DESCRIPTION OF THE INVENTION

The present invention relates to new galenic forms of verapamil with programmed and prolonged release. It concerns galenic forms of this kind which are particularly stable under conditions of elevated temperature such as may occur accidentally in countries of a temperate climate and much more frequently and predictably in countries of a tropical climate. The stability of these new forms lies in their capacity to preserve unchanged both the kinematics of release of verapamil and the total quantity of verapamil released after they have been left under such temperature conditions.

The present invention also relates to medicaments containing these new galenic forms.

An object of the present invention is a new prolonged-release galenic form of verapamil which has excellent verapamil release kinetics and high bioavailability of the verapamil and in which these essential characteristics are completely stable not only when this galenic form is kept at room temperature but also when it is kept at high temperatures, such as temperatures comprised between 45° and 70° C.

According to the present invention, the new galenic prolonged-release forms of verapamil in the form of microgranules containing a pharmacologically acceptable acid-addition salt of verapamil, such as verapamil hydrochloride, as active ingredient, combined with at least one wetting agent are essentially characterized in that these microgranules are coated with a microporous membrane consisting of at least one pharmacologically acceptable adjuvant and at least one film forming mixture composed of at least one polymer of the acrylic and/or methacrylic type insoluble in the organism and at least one substance which may or may not be polymeric but is neither acrylic nor methacrylic and is insoluble in the acid gastric medium but soluble in the intestine.

This microporous membrane enables verapamil to be released by a prolonged action, the kinetics of which are not altered by heating to temperatures of up to 70° C.

According to a feature of the invention, the microgranules contain, in addition to the verapamil salt, at least one wetting agent selected from sugar, polyvinylpyrrolidone, $C_{12}$ to $C_{20}$ fatty acid esters of sucrose or xylose, glycerides of sucrose, fatty acid esters of polyoxythylene, ethers of fatty alcohols and polyoxyethylene, esters of sorbitan, esters of polyoxyethylene sorbitan, and lecithins.

In addition to the wetting agent(s) the microgranules may also contain at least one excipient chosen from the following:
microcrystalline celluloses such as Avicel products (FMC, U.S.A.);
methyl celluloses, ethyl celluloses (Ethocel or Aqua-Coat), carboxymethylcelluloses, hydroxyethyl celluloses (Natrosol, Hercules, U.S.A.), hydroxypropylcelluloses (Klucels, Hercules, U.S.A.);
starches.

According to another feature of the invention, the microporous membrane with which the microgranules containing the verapamil salt are coated consists of a film-forming mixture composed of at least one polymer of the acrylic and/or methacrylic type which is insoluble in the organism and at least one substance which may or may not be polymeric and which is insoluble in the acid gastric medium but soluble in the intestine and is neither acrylic nor methacrylic, the said mixture being combined with at least one pharmaceutically acceptable adjuvant chosen from plasticizers, pigments, fillers, wetting agents, lubricants, anti-static agents and antifoamants.

The microgranules containing the active ingredient are in the form of spheres having diameters in the range of 0.05 to 3 mm, preferably 0.1 mm to 2 mm.

Among the wetting agents present with verapamil hydrochloride in the microgranules, the following in particular may be mentioned:
sucrose, mannitol, sorbitol;
lecithins;
polyvinylpyrrolidones;
$C_{12}$ to $C_{20}$ fatty acid esters of sucrose or sucroesters (Gattefossé, France) and crodestas (Croda, Great Britain);
$C_{12}$ to $C_{20}$ glycerides of sucrose or sucroglycerides;
esters of xylose or xylites;
polyoxyethylene glycerides;
esters of fatty acids and polyoxyethylene (Tefose of Gattefossé, France; Cremophores of BASF, FRG);
ethers of fatty alcohols and polyoxyethylene (Brijs, Renex of Atlas, U.S.A.; Eumulgines of Henkel, FRG);
esters of fatty acids and sorbitan (Spans of Atlas, U.S.A.);
polyoxyethylene esters of fatty acids and sorbitan (Tweens of Atlas, U.S.A.);
glyceride-polyglycides and esters of alcoholpolyglycides (Gelucires of Gattefossé, France).

Among the polymeric and non-polymeric substances which are insoluble in the acid gastric medium but soluble in the intestine may be mentioned in particular cellulose acetophthalate, polyvinyl acetophthalate such as PVAP of Colorcon (U.S.A.), hydroxypropylmethyl cellulose phthalates such as HP 50, HP 55, and HP 55 F of Shin Etsu (Japan), (methylvinyl ether/maleic anhydride) polymers such as Gantrez of GAF (U.S.A.), cholic acids and $C_{10}$ to $C_{20}$ fatty acids.

The polymer or polymers may be combined in the microporous membrane with at least one adjuvant chosen from the following:
plasticizers such as triacetine, dibutyl phthalate, dibutyl sebacate, citric acid esters, polyethylene glycols, polypropylene glycols and polyvinylpyrrolidone;
pigments, optionally coloured, such as oxides of iron and titanium dioxide;
fillers such as lactose and sucrose;
wetting agents such as surface active agents of the type of Span and Tween, namely partial esters of fatty acids (lauric, palmitic, stearic and oleic acid) and hexitol anhydrides derived from sorbitol optionally containing polyoxyethylene chains, preferably surface active agents of the Tween type, in particular Tween 80, and polyethylene glycols;
lubricants such as magnesium stearate and talc;
antifoamants such as silicone oils;
antistatic agents such as colloidal aluminium oxide.

In addition to the polymer or polymers and the substance which is insoluble in the acid gastric medium but soluble in the intestine, the microporous membrane contains, preferably, talc and/or magnesium stearate as lubricant, polyvinyl pyrrolidone as plasticizer, titanium dioxide as pigment. Tween 80 as wetting agent, colloidal aluminium oxide as antistatic agent and silicone oil as antifoamant.

The weight of the microporous membrane may be 2 to 35% and is preferably 5 to 22% of that of the microgranules. The latter may contain verapamil hydrochloride in proportions of 10 to 95% by weight, preferably 30 to 85% by weight.

The microporous membrane may contain 25 to 95%, preferably 30 to 90% of polymer or mixture of polymers.

The invention also relates to a medicament containing verapamil as prolonged release ingredient, said medicament consisting of microgranules containing verapamil, preferably in the form of its hydrochloride, coated with a microporous membrane, these coated microgranules being contained inside capsules, sachets or dose distributors or agglomerated in the form of tablets.

The new galenic forms of verapamil which have delayed release and/or prolonged release in the gastrointestinal tract, are obtained by first preparing the microgranules and then coating them with a microporous membrane.

Various known techniques may be employed for producing the microgranules containing verapamil hydrochloride as described in the copending U.S. patent application of September 1986 in the name of the present Applicants. They may be obtained by spheronisation of an extrudate, by sprinkling and/or spraying in a turbine or in a granulator of the "CF granulator" type, or by mixing in a planetary granulator.

When the dry microgranules have been calibrated to the required diameter by their passage through a suitable sieve, the microporous membrane may be applied by atomisation of the film forming mixture and at least one of the abovementioned adjuvants. This atomisation may be carried out by spraying or pulverising the abovementioned dispersion in a coating turbine or in a fluidised bed apparatus.

According to one exemplary embodiment of the invention, the microporous membrane is obtained from an aqueous dispersion containing, in percentages by weight,
10 to 70% Eudragit E30D (polymer);
5 to 70% hydroxypropylmethyl cellulose phthalate HP 55 F (substance insoluble in acid gastric medium and soluble in the intestine);
1 to 15% talc (lubricant):
1 to 15% polyvinyl pyrrolidone (plasticizer);
0.05 to 2% colloidal aluminium oxide (antistatic agent);

0.01 to 2% Tween 80 (wetting agent);
0.01 to 2% silicone oil (antifoamant);
10 to 70% water (vehicle).

All the characteristics and advantages of the invention will be better understood by the man of the art by reference to the description given below of particular embodiments given by way of non-limiting examples of the new galenic form of verapamil, of the process for its manufacture, and of its therapeutic applications, in particular in relation to pharmacokinetic controls using this new galenic form. Studies of the stability of the release kinetics of these new galenic forms when kept at various temperatures also demonstrate the importance and advantages of the present invention.

EXAMPLES OF PREPARATION OF THE NEW GALENIC FORM

Example 1

1.a. Manufacture of the microgranules

The following ingredients were used:

| | |
|---|---|
| Verapamil HCl | 395 g |
| Sucroester WE 15 (Gattefosse) | 50 g |
| Avicel PH 101* | 50 g |
| Polyvinylpyrrolidone K 30 | 5 g |
| | 500 g |

*microcrystalline cellulose of FMC, U.S.A.

After the aforesaid products had been introduced in powder form into a planetary mixer and granulated by the addition of 75 g of distilled water, the plastic mass obtained was extruded through apertures 1 mm in diameter of the cylindrical die of an extruder (Alexanderwerk). The small cylinders obtained were then made spherical by spheronisation in a Marumerizer type of apparatus. After drying for 24 hours in a ventilated oven heated to 50° C., the fraction of microgranules having a diameter comprised between 0.7 mm and 1.4 mm was recovered by passing the microgranules through a suitable sieve. 437 g of microgranules were thereby obtained (yield: 87%).

1.b. Coating of microgranules 192 g of the following dispersion were sprayed on 400 g of microgranules having a granulometry of from 0.7 to 1.4 mm in a fluidised bed apparatus of Trade Mark Aeromatic, type Strea 1:

| | |
|---|---|
| talc (lubricant) | 50.00 g |
| polyvinylpyrrolidone (plasticizer) | 7.50 |
| Tween 20 (wetting agent) | 0.50 |
| hydroxypropylmethyl cellulose phthalate HP 55 F (enterosoluble substance) | 68.80 |
| Eudragit E30D (insoluble polymer) | 410.80 |
| water | 462.4 |
| | 1000.0 |

Spraying time: 40 minutes
Drying in oven at 50° C. for 24 hours.

1.c. Pharmaceutical forms

After the microgranules had been sieved and their verapamil hydrochloride concentration checked and if necessary adjusted to the desired value by the addition of neutral microgranules such as microgranules of sucrose, the calculated quantity of the mixture was introduced into hard gelatine capsules to provide the desired unit dose of verapamil.

1.d. Investigation of the stability at various temperatures-measurement of the speed of release of verapamil HCl from coated microgranules The quality of the release kinetics of verapamil immediately after manufacture was verified by the method described in "The United States Pharmacopeia (USP) XXI", edition 1985, pp. 1243–1244 under the title "Dissolution Apparatus II", the dissolution medium consisting of a pH 5.8. buffer. A sample of 251.5 mg of microgranules from Example 1 was used for each flask.

Measurement of the dissolution kinetics immediately after manufacture yielded the following results:

| Time | % verapamil HCl dissolved ± SD (Standard Deviation) |
|---|---|
| After 1 h | 5.2 ± 0.2 |
| After 4 h | 36.5 ± 0.7 |
| After 8 h | 61.3 ± 1.2 |

To investigate the stability of the preparation, capsules filled with microgranules from Example 1 were placed in three ovens which were kept at a temperature of 25° C., 50° C. and 70° C., respectively. The dissolution kinetics of verapamil from these capsules were then measured by the aforesaid method of USP XXI.

Figure 4:
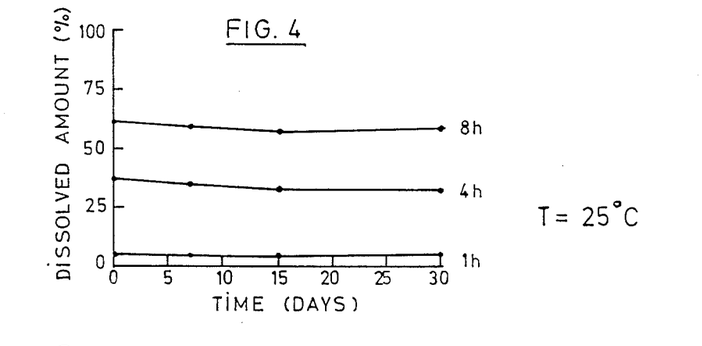
Figure 5:
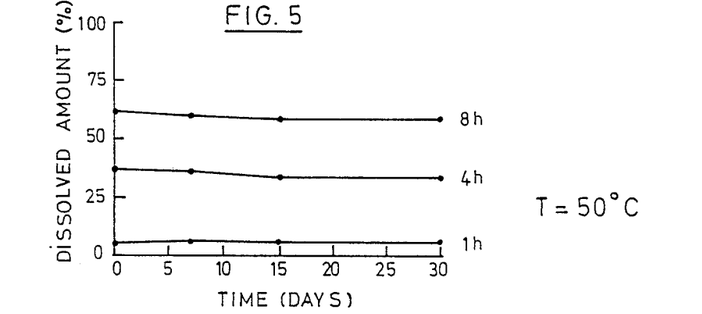
Figure 6:
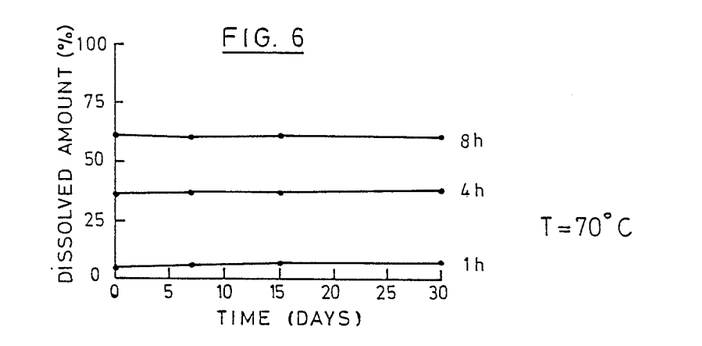

The stability of the kinetics, based on measurements of the percentages of verapamil released after 1 hour, 4 hours and 8 hours, was investigated after the preparation had been stored in the ovens for 7 days, 15 days and 1 month (see appended FIGS. 4, 5 and 6).

Figure 1:
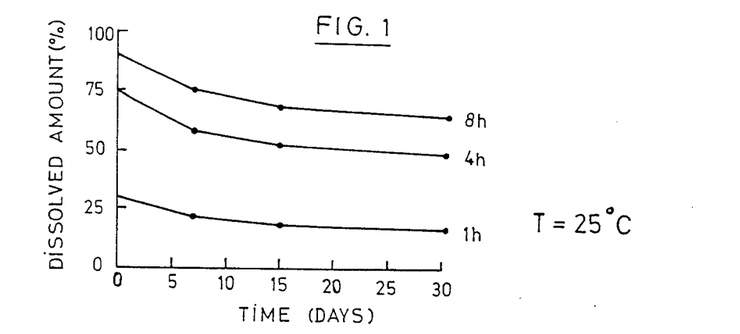
Figure 2:
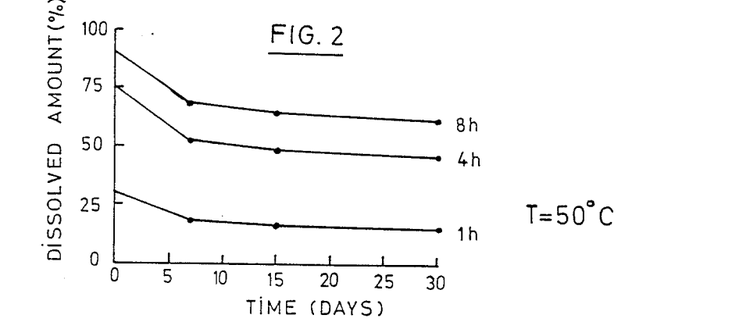
Figure 3:
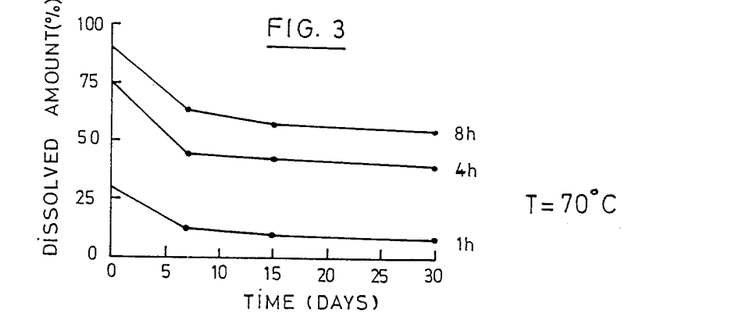

In the context of this investigation, a comparison of FIGS. 1, 2 and 3 with FIGS. 4, 5 and 6 (the microgranules of these two groups only differ in their type of microporous membrane) clearly shows that the new form, which is the object of the present invention, behaves quite differently and in an interesting manner in studies of the stability at elevated temperatures. Whereas the galenic form previously described suffers a very considerable reduction in its release kinetics, the galenic form according to the present invention is found to keep its release kinetics surprisingly constant under the same conditions. The reason for this excellent stability, which is a new and unforeseeable phenomenon, has not been explained to this day.

1.e. Investigation of bioavailability

The new galenic form according to the invention described above was made the object of a detailed pharmacokinetic study in which was compared with an immediate release form (Isoptine ®) and with a prolonged release form at present available on the market (Isoptine Retard ®).

Figure 7:
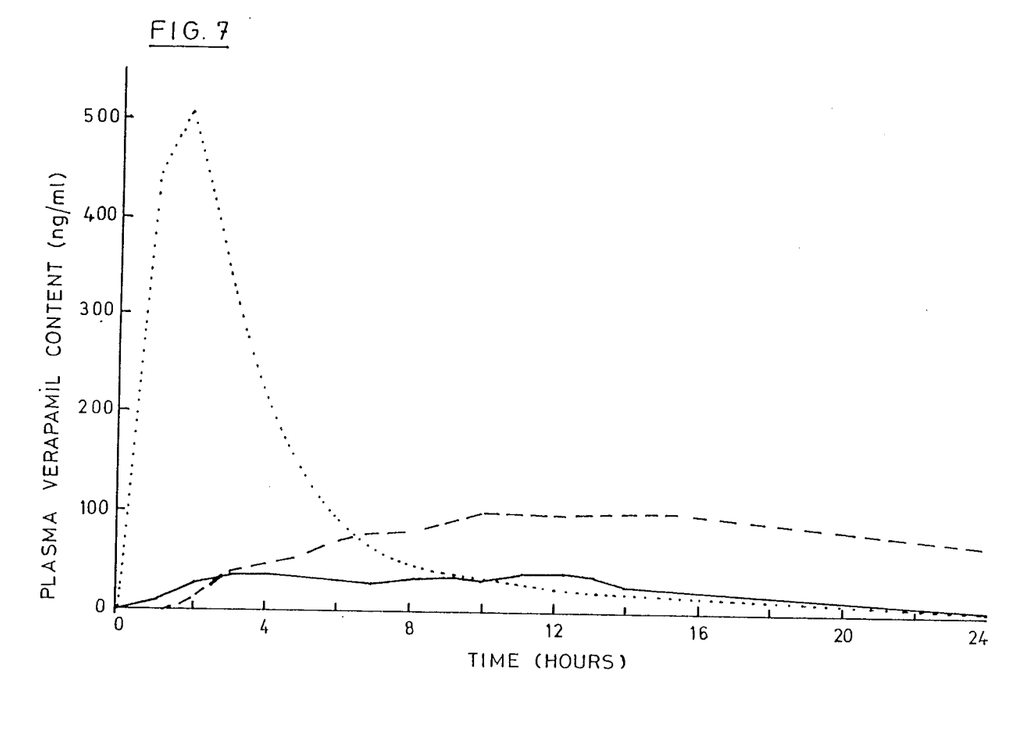

Five healthy volunteers received successively and in a random order each of the three forms at intervals of two weeks and in equivalent doses (360 mg verapamil). The kinetics of the plasma concentrations of verapamil were determined by taking 14 to 16 blood samples, from which the graphs of the appended FIG. 7 were obtained. In FIG. 7, the dotted line curve represents normal isoptine, the curve in broken lines the galenic form according to example 1 and the solid line curve the slow release isoptine known as Isoptine Retard.

The following conclusions may be drawn from this study:

1.e.1. Bioavailability

According to the surface areas under the curves showing the plasma concentrations plotted along the ordinate against the time from 0 to 24 h along the abscissa, the bioavailability of the galenic form from Example 1 is equivalent to that of the immediate release product (since it amounts to 84% of that of the immediate release form even though the values are not extrapolated beyond 24 yours) whereas that of the Isoptine Retard product is substantially lower, amounting to only 26% of that of the rapid release product.

1.e.2. Form and shape of plasma curves

The two prolonged release forms (Example 1 and Isoptine Retard) give rise to virtually parallel curves, the form of which is characteristic of this type of galenic preparation.

Example 2

2.a. Manufacture of microgranules

The following ingredients were used (in grams):

| | |
|---|---|
| Verapamil HCl | 790 |
| Avicel PH 101* | 50 |
| Avicel CL 611* | 50 |
| Polyvinylpyrrolidone K30 | 10 |
| Gelucire 50/13 | 33.30 |
| sucrose | 66.70 |
| | 1000.00 |

*microcrystalline cellulose of FMC, U.S.A.

These ingredients were granulated with 170 ml of water by the same method as in Example 1 but the extruder used was a XTRUDER (Fuji-Paudal). 905 grams of microgranules were obtained (Yield: 90.5%).

2.b. Coating of microgranules

Employing the same procedure as in the preceding example, 322 g of the following dispersion were sprayed on 700 g of microgranules from Example 2:

| | |
|---|---|
| talc (lubricant) | 50.00 |
| polyvinylpyrrolidone (plasticizer) | 7.50 |
| Tween 20 | 0.50 |
| hydroxypropylmethylcellulose phthalate HP 55 F | 87.50 |
| Q.1N sodium hydroxide | 87.50 |
| Eudragit E30D | 348.30 |
| water | 418.70 |

2.c. Pharmaceutical form

The pharmaceutical form was obtained by the method employed in Example 1.

2.d. Measurements of the release kinetics of verapamil and investigation of the stability of the pharmaceutical form at various temperatures Employing the method of Example 1, the results obtained immediately after manufacture were as follows:

| Time | % verapamil dissolved ± SD (n = 3) |
|---|---|
| After 1 h | 9.7 ± 0.15 |
| After 4 h | 54.0 ± 1.07 |
| After 8 h | 80.5 ± 1.50 |

Figure 8:
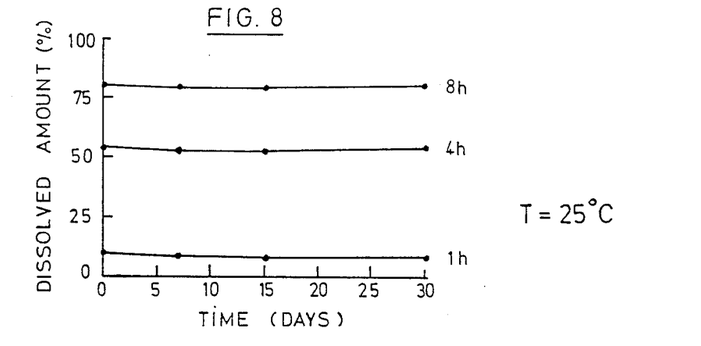
Figure 9:
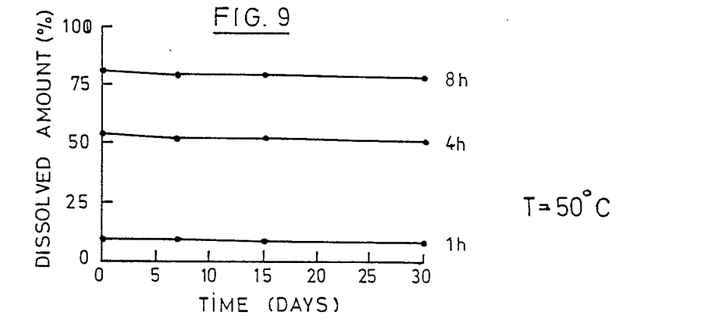
Figure 10:
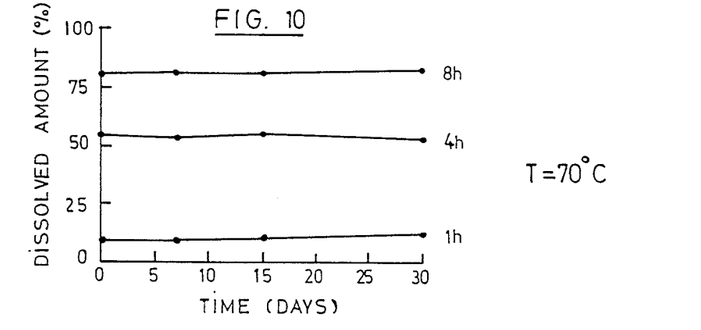

Investigation of the stability at various temperatures was carried out by the same method as in Example 1. The results are shown in FIGS. 8, 9 and 10.

It is clear that the pharmaceutical form of this Example 2 has also very remarkable and equally uneforeseeable characteristics of stability at high temperatures.

2.e. Investigation of bioavailability

Figure 11:
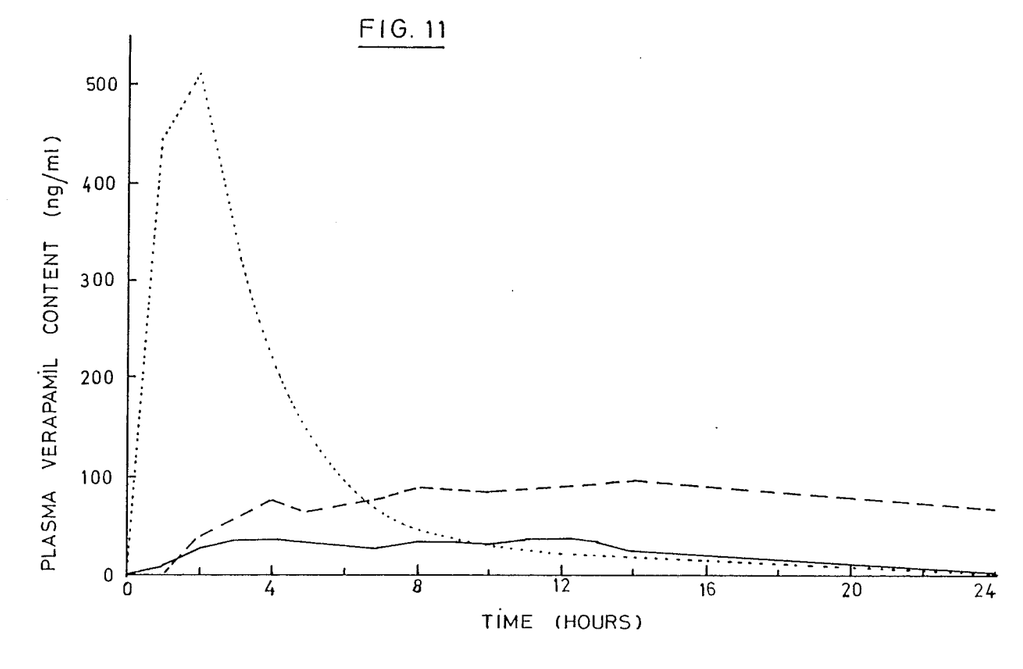

The results of this investigation are presented in FIG. 11. They were obtained by the method employed in Example 1.

The conclusions drawn for this example 2 are the same as for Example 1 and highly remarkable since the following results were obtained:

| | |
|---|---|
| Rapid release form (reference) | 100% |
| Form of Example 2: | 85.9% |
| (Values not extrapolated beyond 24 h) | |

Example 3

3.a. Manufacture of microgranules

The following ingredients were used (in grams):

| | |
|---|---|
| Verapamil HCl | 791 |
| Avicel PH 101* | 55 |
| Avicel Cl 611* | 45 |
| polyvinylpyrrolidone | 9 |
| Crodesta F 160 | 100 |
| | 1000.00 |

These ingredients ware granulated with 170 ml of water by the same method as in Example 1, but the extruder used was a XTRUDER (Fuji-Paudal). 913 grams of microgranules were obtained (yield: 91.3%).

3.b. Coating of microgranules

Employing the same procedure as in the preceding examples, 322 g of the following dispersion were sprayed on 700 g of microgranules from example 3.a:

| | |
|---|---|
| talc (lubricant) | 1000 g |
| polyvinylpyrrolidone (plasticizer) | 150 g |
| Tween 80 | 10 g |
| hydroxypropylmethylcellulose phthalate HP 55 F | 1662 g |
| Antifoam C emulsion* | 30 g |
| Eudragit E30D | 7258 g |
| Water | 9850 g |

*manufactured by Dow Corning (U.S.A.)

3.c. Pharmaceutical form

The pharmaceutical form was obtained by the method employed in example 1.

3.d. Measurement of the release kinetics of verapamil and investigation of the stability of the pharmaceutical form at various temperatures Employing the method of example 1, the results obtained immediately after manufacture were as follows:

| Time | % verapamil HCl dissolved ± SD (n = 3) |
|---|---|
| After 1 h | 9.2 ± 2.9 |
| After 4 h | 65.8 ± 2.1 |
| After 8 H | 93.0 ± 2.2 |

Figure 12:
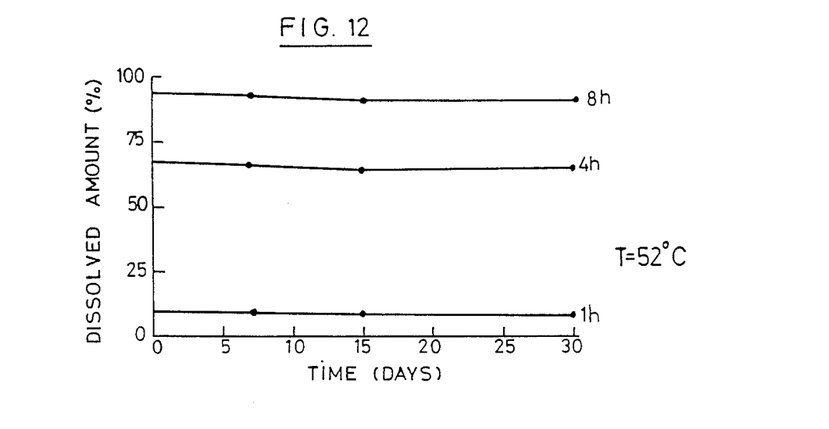
Figure 13:
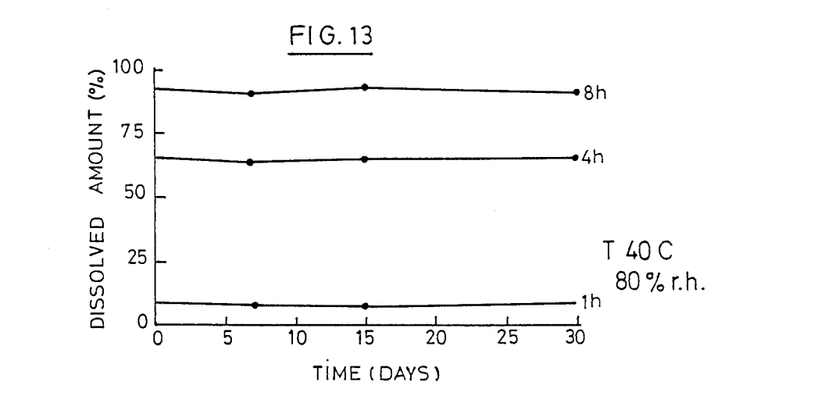

Investigation of the stability at various temperatures was carried out by the same method as in example 1. The results are shown in FIGS. 12 and 13.

It is clear that the pharmaceutical form of this example 3 has also very remarkable and equally unforeseeable characteristics of stability at high temperatures.

As regards the stability, the new galenic forms which constitute the object of the present invention have made it possible to obtain, in a new and unforeseeable manner, a pharmaceutical preparation of prolonged release verapamil with the new and unexpected effects that the characteristics of the dissolution kinetics of verapamil remain constant even if the preparation is kept at temperatures of 25° to 75° C. and that the total quantity of verapamil released from the microgranules and hence available to the organism is preserved.

These properties of stability to heat of the new galenic forms are obviously essential since severe, even temporary, increases in temperature are liable to take place unforseeably if the medicament is kept in the care of the patient or any other person, the effects of such severe temperature increases being not accompanied by any obvious changes in the appearance of the medicament.

Such significant and either fleeting or long lasting rises in temperature may occur, for example, if the bottle containing the medicament is kept close to a source of heat in the home (radiators, summer sunshine through a window or a veranda, etc.) or outdoors, for example in a car left standing in the sunshine while it is transported by the patient or by a medicament supplier.

If random alterations in the properties of the medicament occured, this would obviously be incompatible with effective and reliable therapeutic treatment.

If verapamil were released too slowly, the plasma levels of verapamil would lie below the lower limit of the range of therapeutically effective concentrations. This phenomenon caused by insufficiently rigid release in particularly marked in the case of an active substance such as verapamil in which the short half-life in the plasma is due to rapid metabolisation of the substance. An insufficiently rapid release of the product in the organism is then unable to counterbalance sufficiently the speed of metabolisation, and equilibrium is established at a plasma level which is too low.

Moreover, incomplete release of verapamil from the microgranules results not only in a reduction in bioavailability but also in a reduction in the duration of the therapeutic effect, since release of the fraction which is available takes place over too short a period of time.

In the clinical field, the properties of slow and continuous release of verapamil from microgranules of the new galenic forms according to the present invention have revealed the following important advantages:

The patient can more easily adhere to the prescribed course of treatment since the number of daily doses required is reduced. The new galenic form generally requires to be administrated only once daily whereas an equivalent treatment with quick release preparations requires four daily doses taken once every six hours.

The therapeutic effect is increased: firstly because effective plasma levels are maintained throughout the period between two successive administrations of the medicament, in particular during the night, and secondly because the succession of peaks (temporarily excessively high plasma concentrations) and troughs (excessively low concentrations) is avoided and hence also the undesirable effects of overdosage and lack of therapeutic effect due to underdosage.

The process of adjustment of the individual posology is made easier and its risk reduced due to the considerable reduction in the variations of plasma level from one patient to another.

It may therefore be asserted that the new galenic forms constituting the object of the present invention result in a new medicament which is useful for the treatment of disturbances of cardiac rythm, hypertension and angina pectoris and for any other medical use of verapamil by oral administration.

It is to be understood that the man of the art may find other advantages and variations of the invention, in particular as regards the process of obtaining the microgranules and the membrane which controls the release of the active substance, without thereby departing from the context and scope of the present invention.

What we claim is:

1. A galenic form of verapamil with prolonged release of this compound, consisting of microgranules containing verapamil hydrochloride, as active substance, combined with at least one wetting agent, said microgranules being coated with a microporous membrane consisting of at least one pharmacologically acceptable adjuvant and at least one film-forming mixture comprising at least one of an acrylic and methacrylic polymer which is insoluble in an organism, and a substance which is neither an acrylic nor a methacrylic polymer and which is insoluble in the acid gastric medium but soluble in the intestine of said organism.

2. A galenic form of verapamil according to claim 1, in which the microgranules comprise, at least one wetting agent selected from the group consisting of sugars, polyvinylpyrrolidone, $C_{12}$ to $C_{20}$ fatty acid esters of sucrose or of xylose, glycerides of sucrose, fatty acid esters of polyoxyethylene, ethers of fatty alcohols and polyoxyethylene, esters of sorbitan, esters of polyoxyethylene sorbitan, glyceride-polyglycides, alcohol-polyglycide esters and lecithins.

3. A galenic form of verapamil according to claim 1, in which said microporous membrane further comprises at least one adjuvant selected from the group consisting of plasticizers, pigments, fillers, wetting agents, lubricants, antistatic agents and antifoamants.

4. A galenic form of verapamil according to claim 1, wherein said microgranules are in the form of spheres having a diameter of from 0.05 to 3 mm.

5. A galenic form of verapamil according to claim 1, in which the microgranules contain at least one wetting agent selected form the group consisting of:
sucrose, ammnitol, sorbitol;
lecithins;
polyvinylpyrrolidones;
$C_{12}$ to $C_{20}$ fatty acid esters of sucrose or sucroesters;
$C_{12}$ to $C_{20}$ glycerides of sucrose or sucroglycerides;
esters of xylose or xylites;
polyoxyethylene glycerides;
esters of fatty acids and polyoxyethylene;

ethers of fatty alcohols and polyoxyethylene;
fatty acid esters of sorbitan;
polyoxyethylene esters of fatty acids of sorbitan;
glyceride-polyglycides and esters of alcohol polyglycides.

6. A galenic form of verapamil according to claim 1, in which the insoluble acrylic and/or methacrylic polymer is selected from the group consisting of copolymers of poly(meth)acrylic acid esters and of poly(meth)acrylic acid esters with quaternary ammonium groups.

7. A galenic form of verapamil according to claim 1, in which said substance is selected from the group consisting of cellulose acetophthalate, polyvinyl acetophthalate, hydroxypropyl-methylcellulose phthalates, poly(methyl-vinyl ether/maleic anhydride) products, cholic acids and $C_{10}$ and $C_{20}$ fatty acids.

8. A galenic form of verapamil according to claim 1, in which the microporous membrane coating the microgranules contains, by weight, about 5 to 70% of the film forming mixture, 1 to 15% of talc, 1 to 15% of polyvinyl-pyrrolidone, 0.05 to 2% of colloidal aluminium oxide, 0.01 to 2% of Tween and 0.01 to 2% of silicone oil.

9. A galenic form of verapamil according to claim 1, in which the weight of the microporous membrane is 2 to 35% of that of the microgranules coated by the membrane.

10. A medicament containing verapamil for oral administration, which contains a galenic form of verapamil according to claim 1 in a capsule, a sachet, a dose distributor or a tablet.

11. A medicament containing verapamil for oral administration, which contains a galenic form of verapamil according to claim 2 in a capsule, a sachet, a dose distributor or a tablet.

12. A medicament containing verapamil for oral administration, which contains a galenic form of verapamil according to claim 3 in a capsule, a sachet, a dose distributor or a tablet.

13. A medicament containing verapamil for oral administration, which contains a galenic form of verapamil according to claim 4 in a capsule, a sachet, a dose distributor or a tablet.

14. A medicament containing verapamil for oral administration, which contains a galenic form of verapamil according to claim 5 in a capsule, a sachet, a dose distributor or a tablet.

15. A medicament containing verapamil for oral administration, which contains a galenic form of verapamil according to claim 6 in a capsule, a sachet, a dose distributor or a tablet.

16. A medicament containing verapamil for oral administration, which contains a galenic form of verapamil according to claim 7 in a capsule, a sachet, a dose distributor or a tablet.

17. A medicament containing verapamil for oral administration, which contains a galenic form of verapamil according to claim 9 in a capsule, a sachet, a dose distributor or a tablet.

18. A medicament containing verapamil for oral administration, which contains a galenic form of verapamil according to claim 8 in a capsule, a sachet, a dose distributor or a tablet.

19. A medicament containing verapamil for oral administration, which contains a galenic form of verapamil according to claim 9 in a capsule, a sachet, a dose distributor or a tablet.

20. A medicament according to claim 10, in the form of a unit dose containing 40 to 400 mg of verapamil hydrochloride.

21. A medicament according to claim 11, in the form of a unit dose containing 40 to 400 mg of verapamil hydrochloride.

22. A medicament according to claim 12, in the form of a unit dose containing 40 to 400 mg of verapamil hydrochloride.

23. A medicament according to claim 13, in the form of a unit dose containing 40 to 400 mg of verapamil hydrochloride.

24. A medicament according to claim 14, in the form of a unit dose containing 40 to 400 mg of verapamil hydrochloride.

25. A medicament according to claim 15, in the form of a unit dose containing 40 to 400 mg of verapamil hydrochloride.

26. A medicament according to claim 16, in the form of a unit dose containing 40 to 400 mg of verapamil hydrochloride.

27. A medicament according to claim 17, in the form of a unit dose containing 40 to 400 mg of verapamil hydrochloride.

28. A medicament according to claim 18, in the form of a unit dose containing 40 to 400 mg of verapamil hydrochloride.

29. A medicament according to claim 19, in the form of a unit dose containing 40 to 400 mg of verapamil hydrochloride.

30. A galenic form of verapamil according to any one of claims 1 to 3, in which the adjuvant contained in the microporous membrane is a plasticizer selected from the group consisting of triacetine, dibutylphthalate, dibutyl sebacate, citric acid esters, polyethylene glycols, polypropylene glycols and polyvinylpyrrolidone;
 a pigment selected from the group consisting of oxides of iron and titanum dioxide;
 a filler selected from the group consisting of lactose and sucrose,
 a wetting agent selected from the group consisting of partial esters of fatty acids and of hexitol anhydrides derived from sorbitol, and of polyethylene glycols;
 a lubricant selected from the group consisting of magnesium stearate and talc,
 silicone oil or colloidal aluminium oxide.

31. A galenic form of verapamil according to claim 1, in which the weight of the microporous membrane is 5 to 22% of that of the microgranules coated by the membrane.

32. A galenic form of verapamil according to claim 4, wherein said microgranules are in the form of spheres having a diameter of from 0.1 mm to 2 mm.

* * * * *